United States Patent [19]

Varraux et al.

[11] Patent Number: 4,768,520
[45] Date of Patent: Sep. 6, 1988

[54] PEAK FLOW AND PULMONARY INCENTIVE METER

[76] Inventors: Alan R. Varraux, 5433 Hansel St., Orlando, Fla. 32809; Joseph M. Valdespino, 5023 Golf Club Pkwy., Orlando, Fla. 32808; William M. Hobby, 244 Sylvan Blvd., Winter Park, Fla. 32789

[21] Appl. No.: 417,061

[22] Filed: Sep. 13, 1982

Related U.S. Application Data

[63] Continuation-in-part of Ser. No. 261,022, May 6, 1981, abandoned.

[51] Int. Cl.⁴ .............................................. A61B 5/08
[52] U.S. Cl. .................................................... 128/725
[58] Field of Search .............................. 128/725–730, 128/205.23; 272/99; 116/273; 73/239, 861.56, 861.57

[56] References Cited

U.S. PATENT DOCUMENTS

| | | | |
|---|---|---|---|
| 3,826,247 | 7/1974 | Ruskin et al. | 128/727 |
| 3,871,364 | 3/1975 | Boehringer | 128/727 |
| 3,894,433 | 7/1975 | Riester et al. | 73/861.56 |
| 4,096,855 | 6/1978 | Fleury | 128/727 |
| 4,183,361 | 1/1980 | Russo | 128/725 |

Primary Examiner—Max Hindenburg
Attorney, Agent, or Firm—William M. Hobby

[57] ABSTRACT

An apparatus for measuring peak expiratory flow of a human patient and an incentive spirometer has a housing having a passageway and a mouthpiece connected to the passageway. An elongated slender rod extends through the passageway and has a sliding member a predetermined size slideably mounted thereon adapted to slide on the rod when a patient exhales into the mouthpiece through the passageway. A magnet is attached to the slideable member for sliding therewith to hold the slideable member in position at the maximum position the slideable is raised on the slender rod. The passageway may be tapered in a reverse cone shape making the sliding member more difficult to raise as it moves up the passageway so that patients can lift the slideable member, while most patients cannot lift the member all the way to the top of the passageway. The apparatus serves as an inhalation incentive spirometer by moving the sliding member to the opposite end of the passageway and inhaling through the passageway or by placing a second mouthpiece over the opposite end of the passageway for inhaling through.

19 Claims, 2 Drawing Sheets

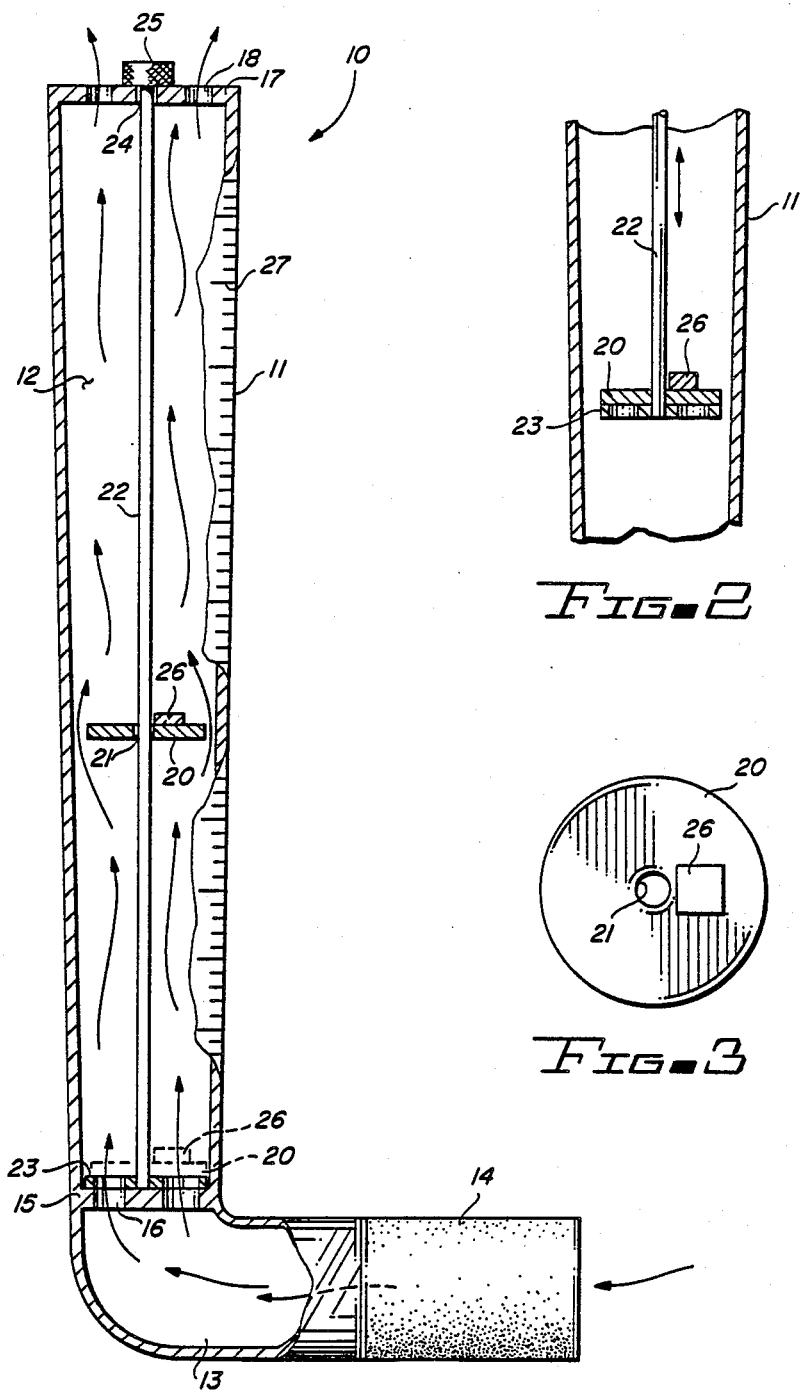

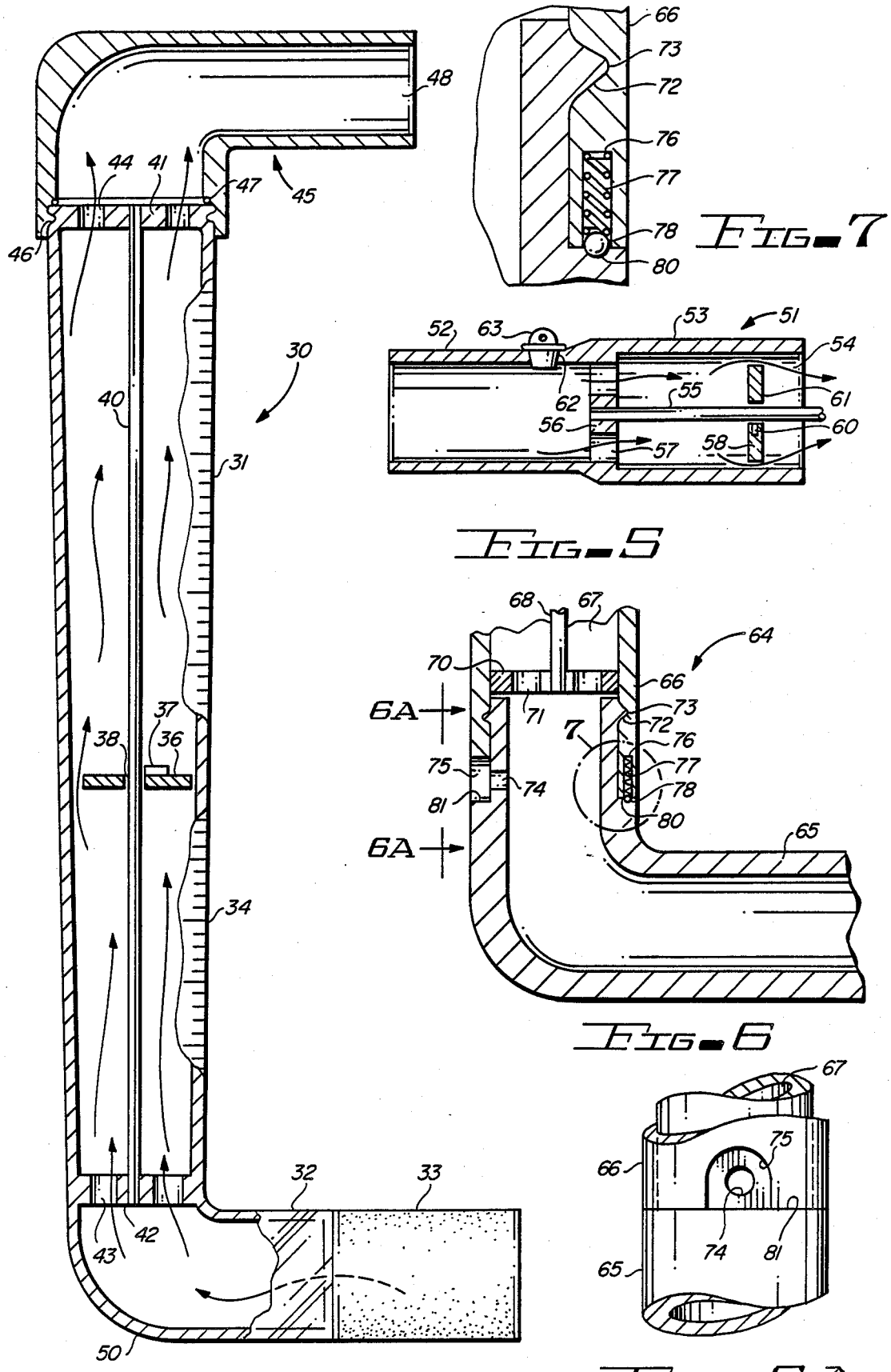

PEAK FLOW AND PULMONARY INCENTIVE METER

This application is a continuation-in-part of our prior patent application Ser. No. 261,022, filed on May 6, 1981, for a Peak Flow Meter, now abandoned.

BACKGROUND OF THE INVENTION

The present invention relates to peak or expiratory flow meters for measuring the maximum exhalation flow rate of a patient.

A peak flow meter is a good general indicator of the presence or absence of airway obstruction and will determine the responsiveness of a patient to bronco dialaters. It is also known that airway obstruction associated with lung diseases is measurable long before symptoms may appear. The measurement of peak expiratory flow is one medical tool for the effective screening of presumably normal subjects away from the hospital and physician's office. Such a device would be particularly useful in factories and as part of health survey programs if an inexpensive peak flow meter was available. In the case of lung diseases, it is particularly important to determine the effectiveness of a prescribed drug without the necessity for hospitalization or constant visits to the physician's office and a peak flow meter may be indicative of the severity of an asthmatic attack.

In the past, expiratory flow meters have frequently been cumbersome or have a complexity of operation prohibiting home use or have lacked sufficient accuracy to be used as a medical screening tool. Frequently, prior art devices do not have a means for holding the peak flow reading, so that it is difficult for a patient to get an accurate reading without someone else watching the meter.

Typically, peak flow meters operate by lifting a ball, cylinder disc, or piston in a tube, which ball is raised by the patient exhaling into the tube to raise the ball. Most such devices do not have provisions for holding the readings of holding the ball at its maximum raised point. Another commonly suggested technique is to have a patient exhale through a passageway having a piston partially blocking the passageway and connected to a spring. This type of device requires special calibration, since the movement of the piston extends or compresses the spring and the force required to extend or compress the spring further is nonlinearly increased. In addition, springs tend to change over a period of time, thereby reducing the accuracy of the measurement.

The present invention is directed towards producing a simplified peak flow meter which can accurately measure the peak expiratory flow of a patient and which can hold the measurement until returned by the patient. Advantageously, the present invention can be used as a pulmonary achievement trainer for patients to practice exhaling into the peak flow meter.

SUMMARY OF THE INVENTION

The present invention relates to a peak flow meter for measuring a patient's peak expiratory flow and has a housing having a passageway therethrough. The passageway may extend vertically or horizontally in the housing and is connected to a generally horizontally extending mouthpiece. A patient exhales into the mouthpiece and through the passageway. An elongated rod extends at least part way through the passageway. A slideable piston member of a predetermined size slides adjacent the elongated rod and has a magnet attached thereto adjacent the elongated rod, whereby blowing into the mouthpiece through the passageway will lift the slideable piston against the force of gravity and against the uniform friction caused by the magnet's attraction to the elongated rod. The piston member is held in position at its peak height by the magnet's attraction to the elongated rod so that the peak flow can be measured along a scale on the housing. In one embodiment, the sliding piston can be returned by raising the elongated rod until the piston engages the passageway top and continuing to raise the rod until the base member engages the elongated rod back into the passageway. The passageway may be tapered to compact the scale by increasing the difficulty of raising the piston. The apparatus may be used as an inhalation spirometer by placing a mouthpiece over the opposite end or by moving the sliding member to the opposite end of the passageway and inhaling through the same mouthpiece used to exhale through.

BRIEF DESCRIPTION OF THE DRAWINGS

Other objects, features and advantages of the present invention will be apparent from the written description and the drawings, in which:

FIG. 1 is a cutaway side perspective view of a peak flow meter in accordance with the present invention;

FIG. 2 is a partial sectional view showing the return of the sliding disc;

FIG. 3 is a top plan view of the sliding disc having a magnet attached thereto;

FIG. 4 is a cutaway side perspective view of another embodiment of a peak flow meter and pulmonary incentive device in accordance with the present invention;

FIG. 5 is a partial sectional view of a horizontal embodiment of a peak flow and pulmonary incentive meter;

FIG. 6 is a partial sectional view of yet another embodiment of a peak flow and pulmonary incentive meter;

FIG. 6A is a partial elevation taken on line 6A—6A of FIG. 6; and

FIG. 7 is a sectional view taken on the circle 7 of FIG. 6.

DESCRIPTION OF THE PREFERRED EMBODIMENTS

Referring to the drawings, a peak flow meter 10 may be used to measure a patient's peak expiratory or exhalation flow rate and has a housing 11 normally held in a vertical direction and having a generally horizontal portion 13 operatively connected thereto with a removable mouthpiece 14. The passageway 12 in the housing 11 is tapered and has a base portion 15 having a plurality of openings 16 therethrough and a top portion 17 having a plurality of openings 18 passing therethrough, so that blowing into the mouthpiece 14 will allow the passage of air through the portion 13, the opening 16, through the passageway 12 and through the openings 18 and out the top 17. A plastic disc or piston 20 has an opening 21 through the center thereof and rides on a slender ferrous rod 22, which has a ferrous perpendicular extending base member 23 attached to one end thereof. The other end of the rod 22 extends out an opening 24 in the top 17 and has a handle portion 25 attached thereto. The disc or piston member 20 has a small magnet 26 attached thereto in a predetermined spaced relationship to the open center portion 21, thereby creating a predetermined magnetic pull against the rod 22.

In operation, a patient inhales and then exhales into the mouthpiece 14 which directs his expiratory flow through the passageway 12, pushing the piston 20 from its position on the base member 23 along the rod 22. The piston 20 is then held at its highest position by the magnet 26 attraction to the slender rod 22, so that a patient can read his peak flow off the graduated scale 27 by the position of the piston 20.

After a measurement is taken, the patent can grasp the handle 25, slide the rod 22 through the opening 24 until the base member 23 engages the piston 20, as shown in FIG. 2. Raising the rod 22 lifts the piston 20 until it reaches the top 17 and forces the piston against the base member 23. The piston 20 is now held by the magnet 26 attraction to the rod 22 adjacent the base 23. Sliding the rod 22 back into the passageway 12 then returns the piston 20 back to the bottom of the passageway as shown in dash lines in FIG. 1. The mouthpiece 14 can then be changed for a different patient. The tapered passageway 12 gradually increases the difficulty of raising the disc 20 as it rises higher by increasing the space around the disc for the flow of the exhaled air. This advantageously compacts the scale 27 so that most patients would be able to move the disc some, but would not be able to drive the disc against the top 17. The patient can then measure his reading on the scale 27 against a chart for his sex, height and age.

Turning now to FIG. 4, an alternate embodiment of a peak flow and pulmonary incentive meter 30 has a transparent housing 31 forming a passageway 35, a mouthpiece portion 32 having a removable mouthpiece 33 thereon. The housing 31 has a scale 34 formed thereon. The piston 36 has a magnet 37 mounted thereon and an aperture 38 therethrough and rides on a ferrous rod 40. The rod 40 has one end attached to a top plate 41 and the other end attached to a bottom plate 42. The bottom plate 42 has a plurality of openings 43 therethrough, while top plate 41 has a plurality of openings 44 therethrough for the passage of air. Blowing into the mouthpiece 33 will direct the air through the openings 43, through the passageway 35 and out the openings 44 to move the piston 37 along the rod 40. Since the magnet exerts a uniform traction to the ferrous rod 40, the resistance to the movement of the piston 36 is uniform over the length of the rod 40. The housing 31 is tapered so as to increase the difficulty of moving the piston 37 as the piston rises in the passageway 35 and thus compacting the scale 34.

An optional inhalation mouthpiece 45 is shown attached to the top of a housing 31 with a large thread 46, such as might require one twist to close a seal 47 against the top 41 to lock the mouthpiece 41 to the top of the housing 31. Inhalation through the passageway 48 will raise the piston 37 similar to blowing through the passageway 32. The piston will maintain its position by the attraction of the magnet 37 to the rod 40 for reading the position of the piston 36 on the scale 34. Piston 36 is returned by merely tapping the bottom 50 of the meter 30 against the palm of the hand. In normal operation, the attachment of the mouthpiece 45 would use the meter held in a horizontal position while exhalation through the mouthpiece 32 will be in a vertical direction. Holding the meter on a horizontal during inhaling slightly reduces the difficulty in moving the piston 36 and avoids shifting of the piston 36 from the sudden movement that is frequently accompanied with inhalation through a mouthpiece.

Referring to FIG. 5, a partial sectional view of another embodiment of a peak flow and pulmonary incentive meter 51 has a mouthpiece 52 connected axially to the housing 53 forming the passageway 54. In this case, a ferrous rod 55 is fixedly attached to a base 56 having a plurality of openings 57 therein and is attached to the other end of the passageway 54 in the same manner as shown in FIG. 4. A piston 58 may be made of a polymer material and may have a magnet 60 embedded therein and an aperture 61 therethrough so that the piston 58 rides on the ferrous rod 55. In this embodiment, inhaling or exhaling through the mouthpiece 52 will allow the meter to be used as a peak flow meter during exhalation and as an incentive spirometer during inhalation or exhalation. The piston 58 needs to be returned to the starting position against the base 56 prior to exhalation and shifted to the other end adjacent the top for inhalation through the mouthpiece 52. Both operations take place while holding the meter horizontally and since the magnetic attraction from the magnet 60 is uniform along the rod 55, a linear scale may be used, especially since the housing 53 in this case is cylindrical. Since the housing 53 is not tapered, a very long passageway 54 is required to obtain reading from a wide variety of patients for both inhalation or exhalation. One or more openings 62 may have removable plugs 63 therein. When the plug 63 is removed, air is released through the opening 62, thereby reducing the flow through the passageway 54 in a uniform manner and thus allowing two or more scales to be used on the housing 30.

A similar result is obtained in the embodiment of FIGS. 6, 6A and 7, which has a peak flow and incentive meter 64 having a mouthpiece 65 which normally would be held in a horizontal or vertical position, as desired. Passageway 67 in the housing 66 has a ferrous rod 68 mounted to a bottom member 70 having a plurality of openings 71 therein and is mounted to the top in the same manner as shown in FIG. 4. Mouthpiece 65 has an annular lip 72 riding in an annular groove 73 to allow the mouthpiece 65 to be rotated on the housing 66. The mouthpiece 65 has one or more openings 74 therethrough which can align with an opening or a niche 75 in the bottom of the housing 66. A small bore 76 in the housing 66 has a spring 77 therein with a ball-bearing click 78 mounted to the bottom thereof for fitting into small recesses 80 positioned along the ledge 81 of mouthpiece 65, to thereby align the opening 74 with the opening 75 or blocking the opening 74 with the housing 66. The recesses 80 can be aligned so that a plurality of scales on the housing 66 will always have the appropriate scale aligned with the direction of the mouthpiece 65 so that a patient inhaling or exhaling through the mouthpiece 65 can look directly at the appropriate scale. The meter is, of course, calibrated to measure peak flow during exhalation but may be used as an incentive by measuring the exhalation since the larger the inhalation before exhaling through the peak flow meter, the greater the pistion 70 can be moved up the passageway 67.

It should be clear at this time that a peak expiratory flow meter and inhalation incentive spirometer has been provided which is simple in operation and which can be inexpensively manufactured and used. However, further uses and changes are contemplates, such as using different size pistons 20, 36 and 50, or openings in the pistons can be used to vary the difficulty of operation for different patients by varying the space around or through each piston. Accordingly, the present invention is not to be construed as limited to the forms shown, which are to be considered as illustrative rather than restrictive.

I claim:

1. A pulmonary apparatus comprising in combination:
   a housing having a passageway therethrough having a top portion and a bottom portion;
   a mouthpiece connected to said housing and to said passageway adapted for a patient to breath through the mouthpiece and through the passageway;
   elongated rod extending through at least a portion of said passageway;
   a piston member movably mounted adjacent said elongated rod and adapted to move responsive to the passage of gas through said passageway, said housing passageway being tapered to increase the size of the passageway relative to the movable piston as the movable piston is raised from a starting position and said movable piston being a slideable disc having an aperture therein with said elongated rod extending through said aperture; and
   magnet means forming a part of said piston member for sliding therewith, said magnet means being positioned in a predetermined spaced relationship to said elongated rod whereby said magnet means supports said piston to indicate the peak position said piston is moved by a patient breathing through said passageway.

2. The apparatus in accordance with claim 1, in which said elongated rod has a base portion on one end thereof located in said housing passageway and a means to grip said elongated rod on the other end thereof located outside said housing.

3. The apparatus in accordance with claim 2, in which said elongated rod is slideably mounted through a housing top portion, whereby raising said elongated rod will pull said movable piston member held by said magnet means upward to engage the top portion of said passageway and will allow the elongated rod to continue sliding until the base portion on one end of said elongated rod abust against said disc, whereby sliding said elongate rod back into said housing passageway will return said movable disc to a starting position.

4. The apparatus in accordance with claim 1, in which said mouthpiece includes a removable mouthpiece.

5. The apparatus in accordance with claim 1, in which said housing passageway has a bottom having a plurality of openings therethrough and the housing top portion has a plurality of openings therethrough.

6. The apparatus in accordance with claim 5, in which said housing forming said passageway is transparent and has a plurality of graduations formed thereon.

7. The apparatus in accordance with claim 1, in which said magnet means includes a permanent magnet fixedly attached to said piston member in a predetermined position.

8. A pulmonary apparatus in accordance with claim 1, in which said mouthpiece is rotatably mounted to said housing to position said mouthpiece to open an aperture in said passageway in a predetermined position and to block said aperture in a second predetermined to thereby vary the flow passing by said piston by releasing or blocking the flow through an auxiliary opening in the side of said passageway.

9. A pulmonary apparatus in accordance with claim 8, in which said mouthpiece and housing has click stop to position said mouthpiece relative to said housing.

10. A pulmonary apparatus in accordance with claim 9, in which said housing has a plurality of scales thereon, each positioned to be aligned with one click stop aligned with a predetermined position of said mouthpiece.

11. A pulmonary apparatus in accordance with claim 10, in which said elongated rod extending through at least a portion of said passageway is fixedly attached to a bottom and top plate mounted at either end of said passageway.

12. A pulmonary apparatus in accordance with claim 1, in which said mouthpiece has at least one auxiliary opening therethrough having removable blocking means therein.

13. A pulmonary apparatus in accordance with claim 1, in which said mouthpiece is mounted on the same axis as said housing passageway.

14. A pulmonary apparatus in accordance with claim 1, including a second mouthpiece removably attachable to said housing on the opposite end from said mouthpiece to provide an inhalation port on the end of said passageway.

15. A pulmonary apparatus in accordance with claim 14, in which said second mouthpiece is threadedly attached to one end of said housing and has a seal formed thereon.

16. A pulmonary apparatus comprising in combination:
   transparent housing forming a passageway therein;
   piston means movably positioned in said housing passageway and sized for air to flow thereby upon a patient inhaling or exhaling through said housing passageway;
   an elongated member extending through at least a portion of said passageway;
   magnet means positioned in said housing passageway to hold said piston means in place to said elongated member in said passageway at the peak point said piston is moved in said passageway, said magnet means being attached to said piston means to hold said piston in the maximum position lifted by a patient exhaling into said passageway by the magnet means attraction to said elongated member;
   a first mouthpiece for a patient to exhale through into said housing passageway to drive said piston in said passageway; and
   a second mouthpiece removably attachable to said housing for a patient to inhale air through thereby drawing air through said housing passagway.

17. A pulmonary apparatus in accordance with claim 16, in which said first mouthpiece is attached to one end portion of said transparent housing and said first mouthpiece is attached to the other end portion of said housing, whereby a patient may exhale through one mouthpiece and inhale through the other.

18. A pulmonary apparatus in accordance with claim 17, in which one said mouthpiece means mouthpiece is actually aligned with said transparent housing passageway.

19. A pulmonary apparatus in accordance with claim 18, in which said mouthpiece means is rotatably attached to said transparent housing to position said mouthpiece to open an aperture into said passageway in one position and to close said aperture when said mouthpiece is rotated to said second position to thereby vary the flow past said piston or opening or closing an auxiliary aperture to said passageway.

* * * * *